(12) United States Patent
Cunningham et al.

(10) Patent No.: US 10,500,136 B2
(45) Date of Patent: Dec. 10, 2019

(54) SYSTEMS, METHODS AND COMPUTER PROGRAM PRODUCTS FOR ASSIGNING TIMES OF ADMINISTRATION TO PRESCRIPTION MEDICATIONS

(71) Applicant: Parata Systems, LLC, Durham, NC (US)

(72) Inventors: Paul Joseph Cunningham, Hillsborough, NC (US); Andrew Keller McCarron, Raleigh, NC (US)

(73) Assignee: PARATA SYSTEMS, LLC, Durham, NC (US)

( * ) Notice: Subject to any disclaimer, the term of this patent is extended or adjusted under 35 U.S.C. 154(b) by 273 days.

(21) Appl. No.: 15/496,333

(22) Filed: Apr. 25, 2017

(65) Prior Publication Data

US 2017/0224589 A1   Aug. 10, 2017

Related U.S. Application Data

(62) Division of application No. 14/265,945, filed on Apr. 30, 2014, now Pat. No. 9,694,966.

(51) Int. Cl.
*G06F 19/00* (2018.01)
*A61J 7/04* (2006.01)
(Continued)

(52) U.S. Cl.
CPC ............ *A61J 7/0409* (2013.01); *B65D 83/04* (2013.01); *B65D 83/0409* (2013.01); *G05B 15/02* (2013.01); *G06F 19/3462* (2013.01)

(58) Field of Classification Search
CPC .... G06Q 50/00; G06Q 10/00; G06F 19/3462; G06F 19/00
See application file for complete search history.

(56) References Cited

U.S. PATENT DOCUMENTS 7,765,491 B1   7/2010   Cotterill
7,996,243 B1   8/2011   Ali et al.
(Continued)

FOREIGN PATENT DOCUMENTS

WO   WO 2007/127359 A2   11/2007

OTHER PUBLICATIONS

Office Action, Canadian Patent Application No. 2,850,816, dated Jan. 6, 2016, 6 pages.

*Primary Examiner* — Mahelet Shiberou
(74) *Attorney, Agent, or Firm* — Myers Bigel, P.A.

(57) ABSTRACT

Methods, systems, and computer program products for assigning times of administration to patient medications are described. A GUI is displayed within a display associated with a pharmaceutical dispensing system. The GUI includes a one day time scale for assigning a time of administration for the medication. One or more daily times of administration for the medication are assigned in response to user input via the one day time scale. A dose of the medication is packaged in each of a respective plurality of pouches according to the assigned daily times of administration via the pharmaceutical dispensing system. The one day time scale may include a time line representative of a twenty-four hour period and one or more time indicators that are positionable by a user. The one day time scale may include a plurality of food consumption times, each selectable by a user for assigning a time of administration.

9 Claims, 9 Drawing Sheets

(51) Int. Cl.
*B65D 83/04* (2006.01)
*G05B 15/02* (2006.01)

(56) References Cited

U.S. PATENT DOCUMENTS

| | | |
|---|---|---|
| 8,032,393 B2 | 10/2011 | Palazzolo et al. |
| 8,181,119 B1 | 5/2012 | Ording |
| 8,244,557 B1 | 8/2012 | Nadas et al. |
| 8,249,890 B1 | 8/2012 | Nadas et al. |
| 8,275,634 B2 | 9/2012 | Palazzolo et al. |
| 8,311,853 B1 | 11/2012 | Pankow et al. |
| 8,364,503 B1 | 1/2013 | Biesenthal et al. |
| 9,235,701 B2 * | 1/2016 | Wu .................. G06F 21/44 |
| 2004/0093252 A1 | 5/2004 | Maekawa |
| 2005/0080650 A1 | 4/2005 | Noel |
| 2008/0059228 A1 | 3/2008 | Bossi et al. |
| 2009/0281835 A1 | 11/2009 | Patwardhan et al. |
| 2011/0000170 A1 | 1/2011 | Burg et al. |
| 2012/0192108 A1 | 7/2012 | Kolb |
| 2013/0341343 A1 | 12/2013 | Lomenick |

\* cited by examiner

HCA MANAGEMENT

| PASS | PATIENT NAME | DATE OF BIRTH |
|---|---|---|
| ☐ | DOE, BOB | 2/18/1998 |
| ☐ | DOE, EVE | 5/27/2005 |
| ☐ | DOE, JANE | 1/21/1985 |
| ☐ | DOE, JOHN | 1/1/1980 |
| ☐ | DUPONT, JEAN | 2/14/1965 |
| ☐ | JONES, MARY | 2/10/1955 |
| ☐ | JONES, TIM | 2/2/1950 |
| ☐ | NYORO, NYORO | 12/31/2005 |
| ☐ | PALLINO, MARIA | 6/16/1953 |
| ☐ | PETROVICH, IVAN | 10/31/1963 |

PATIENT QUERY

SEARCH BY
▽ PATIENT NAME

FIRST NAME...

LAST NAME...

☐ DISPLAY PASS PATIENT ONLY

RETURN TO FULL LIST

SEARCH

◁◁ ◁ PAGE 1 OF 2 ▷ ▷▷

SELECT

SYSTEMS, METHODS AND COMPUTER PROGRAM PRODUCTS FOR ASSIGNING TIMES OF ADMINISTRATION TO PRESCRIPTION MEDICATIONS

RELATED APPLICATION

This application is a divisional application of pending U.S. patent application Ser. No. 14/265,945, filed Apr. 30, 2014, the disclosure of which is incorporated herein by reference as if set forth in its entirety.

RESERVATION OF COPYRIGHT

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

FIELD OF THE INVENTION

The present invention relates generally to the dispensing of prescriptions of pharmaceuticals and, more particularly, to methods, systems and computer program products for automated dispensing of pharmaceuticals.

BACKGROUND

For many people, taking multiple medications can be confusing due to the similarity of pills and varying frequency of administration. Moreover, it may be difficult for a person to remember whether he/she has already taken a particular medication, and whether it needed to be taken with a meal or separately from other medications. In hospitals and long term care facilities having many patients, this may be even more difficult to manage as the number of medications being administered can easily be confused.

To address the administration of multiple medications, strip packaging has been developed wherein medications are packaged in individual pouches for administration at a specific date and time of day. Typically, these pouches are removably joined together and often provided in rolls. The pouches can be separated from the roll when needed at a particular time of day. For example, FIG. 1 illustrates a conventional strip packaging pouch 10 containing a plurality of medications 12 therein. Various information is displayed on a surface 10a of the pouch 10, including patient identification information 14, time of administration information 16, medication identification, quantity, and strength information 18, special directions 20, and a bar code 22, such as for bedside scanning.

As automated pharmacy machines for preparing strip packaging have become substantially more robust and complex, operating software that is correspondingly robust may be needed to facilitate user interaction and control of these machines for producing such packaging.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Embodiments of the present invention provide methods, systems, and computer program products for packaging prescribed patient medications to be taken over a period of time. Embodiments of the present invention are patient-centric and allow medications to be assigned times of administration that best fit with a patient's schedule, lifestyle, etc. In addition, for medications that are to be taken with food, embodiments of the present invention allow such medications to be assigned to specific meals or snack periods during the day.

For example, in some embodiments of the present invention, a method of packaging a prescribed patient medication to be taken over a period of time includes displaying a graphical user interface (GUI) within a display associated with a pharmaceutical dispensing system, wherein the GUI comprises a one day time scale for assigning a time of administration for the medication, assigning one or more daily times of administration for the medication in response to user input via the one day time scale, and packaging a dose of the medication in each of a respective plurality of pouches according to the assigned daily times of administration via the pharmaceutical dispensing system. Each pouch typically displays an identification of the medication contained therein and a date and time of administration for the medication.

In some embodiments, the one day time scale includes a time line representative of a twenty-four hour period. The GUI includes one or more time indicators that are positionable (e.g., slidably positionable, etc.) by a user at a respective time on the time line for assigning a time of administration of a dose of the medication. In some embodiments, the GUI includes a pair of time indicators that are spaced apart by a selected time period such that movement of one of the time indicators automatically causes the other time indicator to move to maintain the selected time period therebetween.

In other embodiments, the one day time scale includes a plurality of food consumption times, wherein each food consumption time is selectable by a user for assigning a time of administration of a dose of the medication. In some embodiments the one day time scale includes an arcuate display having a plurality of user-configurable segments (e.g., number of segments, description of segments, etc.), each segment corresponding to a respective one of the food consumption times. Exemplary segments include a breakfast segment, a lunch segment, an afternoon snack segment, a dinner segment, and a bedtime snack segment. Each segment is responsive to user actuation for assigning a time of administration to a dose of the medication.

In other embodiments, the GUI includes one or more user input boxes, wherein each user input box is associated with a time of day or a food consumption time. Each user input box is configured to receive a number representative of the quantity of the medication that is to be taken at a respective time of day or food consumption time.

In other embodiments, the GUI includes a calendar GUI that comprises an array of blocks representative of the days of a month. Each block is configured to display one or more times of day and/or one or more food consumption times and a quantity of the medication that is to be taken at a respective time of day or food consumption time. A user assigns a time of administration of a dose of the medication for one or more of the blocks via the second GUI.

According to other embodiments of the present invention, a method of packaging a plurality of prescribed patient medications to be taken over a period of time includes displaying a first GUI within a display associated with a pharmaceutical dispensing system, wherein the first GUI contains prescription information for each of the medications that can be taken together (e.g., medication identification, medication quantity, and medication dose amount, etc.). The first GUI also includes a time picker GUI control that is responsive to user actuation for displaying a second GUI that includes a one day time scale for assigning a time of administration for each of the medications.

For each medication, the second GUI is displayed in response to user actuation of the time picker GUI control, and one or more daily times of administration for the medication are assigned in response to user input via the one day time scale. Individual doses of the medications are then packaged in a plurality of pouches via the pharmaceutical dispensing system. Each pouch contains an individual dose of a plurality of the medications having the same daily time of administration, and each pouch typically displays an identification of the medications contained therein and a date and time of administration for the medications. In some embodiments, a third GUI is displayed adjacent to the first GUI that includes a representation of each of the plurality of pouches. Each pouch representation may contain an identification of the medications contained in the corresponding pouch and a date and time of administration for the medications in the corresponding pouch.

In some embodiments, the second GUI includes a time line representative of a twenty-four hour period, and one or more time indicators. Each time indicator is positionable (e.g., slidably positionable, etc.) by a user at a respective time on the time line for assigning a time of administration of a dose of a respective medication. In some embodiments, the GUI includes a pair of time indicators that are spaced apart by a selected time period such that movement of one of the time indicators automatically causes the other time indicator to move to maintain the selected time period therebetween.

In some embodiments, the second GUI comprises a plurality of food consumption times, wherein each food consumption time is selectable by a user for assigning a time of administration of a dose of a respective medication. In some embodiments, the second GUI includes an arcuate display having a plurality of user-configurable segments (e.g., number of segments, description of segments, etc.), each segment corresponding to a respective one of the food consumption times. Exemplary segments include a breakfast segment, a lunch segment, an afternoon snack segment, a dinner segment, and a bedtime snack segment. Each segment is responsive to user actuation for assigning a time of administration of a dose of a respective medication.

In other embodiments, the second GUI includes one or more user input boxes, wherein each user input box is associated with a time of day or a food consumption time. Each user input box is configured to receive a number representative of a quantity of the medication that is to be taken at a respective time of day or food consumption time.

In other embodiments, a fourth GUI is provided that comprises an array of blocks representative of the days of a month. Each block is configured to display one or more times of day and/or one or more food consumption times and a quantity of the medication that is to be taken at a respective time of day or food consumption time. A user assigns a time of administration of a dose of the medication for one or more of the blocks via the second GUI.

According to other embodiments of the present invention, a pharmaceutical dispensing system includes a user station and a packaging station that is configured to selectively package individual doses of medication into customized packaging, such as pouches/strip packaging. A processor is connected to the user station and the packaging station and communicates with a memory that stores instructions to be executed by the processor. These instructions cause the processor to display a GUI within a display associated with the user station, wherein the GUI comprises a one day time scale for assigning a time of administration for the medication, assign one or more daily times of administration for the medication in response to user input via the one day time scale, and package a dose of the medication in each of a respective plurality of pouches according to the assigned daily times of administration via the packaging system. Each pouch typically displays an identification of the medication contained therein and a date and time of administration for the medication.

In some embodiments, the one day time scale includes a time line representative of a twenty-four hour period. The GUI includes one or more time indicators that are positionable (e.g., slidably positionable, etc.) by a user at a respective time on the time line for assigning a time of administration of a dose of the medication. In some embodiments, the GUI includes a pair of time indicators that are spaced apart by a selected time period such that movement of one of the time indicators automatically causes the other time indicator to move to maintain the selected time period therebetween.

In other embodiments, the one day time scale includes a plurality of food consumption times, wherein each food consumption time is selectable by a user for assigning a time of administration of a dose of the medication. In some embodiments the one day time scale includes an arcuate display having a plurality of user-configurable segments (e.g., number of segments, description of segments, etc.), each segment corresponding to a respective one of the food consumption times. Exemplary segments include a breakfast segment, a lunch segment, an afternoon snack segment, a dinner segment, and a bedtime snack segment. Each segment is responsive to user actuation for assigning a time of administration to a dose of the medication.

In other embodiments, the GUI includes one or more user input boxes, wherein each user input box is associated with a time of day or a food consumption time. Each user input box is configured to receive a number representative of a quantity of the medication that is to be taken at a respective time of day or food consumption time.

In other embodiments, the GUI includes a calendar GUI that comprises an array of blocks representative of the days of a month. Each block is configured to display one or more times of day and/or one or more food consumption times and a quantity of the medication that is to be taken at a respective time of day or food consumption time. A user assigns a time of administration of a dose of the medication for one or more of the blocks via the second GUI.

According to other embodiments of the present invention, a pharmaceutical dispensing system includes a user station and a packaging station that is configured to selectively package individual doses of medication into customized packaging, such as pouches/strip packaging. A processor is connected to the user station and the packaging station and communicates with a memory that stores instructions to be executed by the processor. These instructions cause the processor to display a first GUI within a display associated with the user station, wherein the first GUI contains prescription information for each of the medications that can be taken together (e.g., medication identification, medication quantity, and medication dose amount, etc.). The first GUI also includes a time picker GUI control that is responsive to user actuation for displaying a second GUI that includes a one day time scale for assigning a time of administration for each of the medications.

The instructions further cause the processor to display the second GUI in response to user actuation of the time picker GUI control, and assign one or more daily times of administration for the medication in response to user input via the one day time scale. The instructions further cause the processor to package individual doses of the medications in a plurality of pouches via the packaging station. Each pouch contains an individual dose of a plurality of the medications having the same daily time of administration, and each pouch typically displays an identification of the medications contained therein and a date and time of administration for the medications.

In some embodiments, the instructions further cause the processor to display a third GUI adjacent to the first GUI, wherein the third GUI displays a representation of each of the plurality of pouches. Each pouch representation may contain an identification of the medications contained in the corresponding pouch and a date and time of administration for the medications in the corresponding pouch.

In some embodiments, the second GUI includes a time line representative of a twenty-four hour period, and one or more time indicators. Each time indicator is positionable (e.g., slidably positionable, etc.) by a user at a respective time on the time line for assigning a time of administration of a dose of a respective medication. In some embodiments, the GUI includes a pair of time indicators that are spaced apart by a selected time period such that movement of one of the time indicators automatically causes the other time indicator to move to maintain the selected time period therebetween.

In some embodiments, the second GUI comprises a plurality of food consumption times, wherein each food consumption time is selectable by a user for assigning a time of administration of a dose of a respective medication. In some embodiments, the second GUI includes an arcuate display having a plurality of user-configurable segments (e.g., number of segments, description of segments, etc.), each segment corresponding to a respective one of the food consumption times. Exemplary segments include a breakfast segment, a lunch segment, an afternoon snack segment, a dinner segment, and a bedtime snack segment. Each segment is responsive to user actuation for assigning a time of administration of a dose of a respective medication.

In other embodiments, the second GUI includes one or more user input boxes, wherein each user input box is associated with a time of day or a food consumption time. Each user input box is configured to receive a number representative of a quantity of the medication that is to be taken at a respective time of day or food consumption time.

In other embodiments, a fourth GUI is provided that comprises an array of blocks representative of the days of a month. Each block is configured to display one or more times of day and/or one or more food consumption times and a quantity of the medication that is to be taken at a respective time of day or food consumption time. A user assigns a time of administration of a dose of the medication for one or more of the blocks via the second GUI.

According to other embodiments of the present invention, a computer program product includes a non-transitory computer readable storage medium having encoded thereon instructions that, when executed on a processor, cause the processor to display a GUI within a display associated with a pharmaceutical dispensing system, wherein the GUI comprises a one day time scale for assigning a time of administration for the medication. The instructions further cause the processor to assign one or more daily times of administration for the medication in response to user input via the one day time scale, and package a dose of the medication in each of a respective plurality of pouches according to the assigned daily times of administration via the pharmaceutical dispensing system. Each pouch typically displays an identification of the medication contained therein and a date and time of administration for the medication.

According to other embodiments of the present invention, a computer program product includes a non-transitory computer readable storage medium having encoded thereon instructions that, when executed on a processor, cause the processor to display a first graphical user interface (GUI) within a display associated with a pharmaceutical dispensing system, wherein the first GUI contains prescription information for each of the medications that can be taken together (e.g., medication identification, medication quantity, and medication dose amount, etc.). The first GUI also includes a time picker GUI control that is responsive to user actuation for displaying a second GUI that includes a one day time scale for assigning a time of administration for each of the medications.

The instructions further cause the processor to display the second GUI in response to user actuation of the time picker GUI control, and assign one or more daily times of administration for the medication in response to user input via the one day time scale. The instructions further cause the processor to package individual doses of the medications in a plurality of pouches via the packaging station. Each pouch contains an individual dose of a plurality of the medications having the same daily time of administration, and each pouch typically displays an identification of the medications contained therein and a date and time of administration for the medications.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate some exemplary embodiments. The drawings and description together serve to fully explain the exemplary embodiments.

FIGS. 3-9 are graphical user interfaces (GUIs) that allow an operator of an automated pharmaceutical dispensing system to package multiple medications in individual multi-dose medication pouches, according to some embodiments of the present invention.

DETAILED DESCRIPTION

Figure 1:
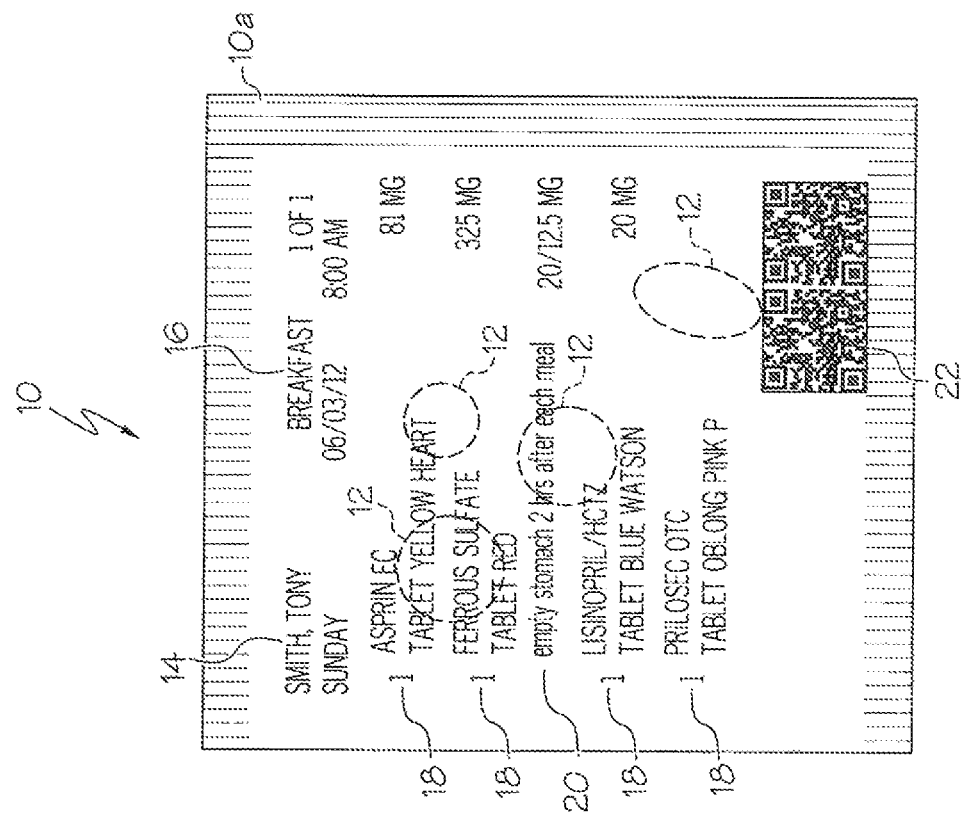
FIG. 1 illustrates a multi-dose medication pouch that may be utilized in accordance with embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain components or features may be exaggerated for clarity, and broken lines may illustrate optional features or elements unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will also be understood that, although the terms first, second, etc. may be used herein to describe various elements, these elements should not be limited by these terms. These terms are only used to distinguish one element from another. For example, a first GUI control could be termed a second GUI control, and, similarly, a second GUI control could be termed a first GUI control without departing from the teachings of the disclosure.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary by +/−20%, 10%, 5%, 1%, 0.5%, or even 0.1%.

The terms "container" and "pouch", as used herein, refer to any type of container that may be utilized to contain multiple medications that are to be taken at the same time of day.

The term "pharmaceutical dispensing system", as used herein, refers to any type of pharmaceutical dispensing system including, but not limited to, automated systems that fill containers/pouches with pills, and semi-automated systems that fill containers/pouches with pills.

The terms "pharmaceutical" and "medication", as used herein, are interchangeable and refer to medicaments prescribed to patients.

The term "pills" refers to any type of medicament that can be packaged within a container/pouch by automated and semi-automated pharmacy systems including, but not limited to, capsules, tablets, caplets, gel caps, lozenges, and the like.

The terms "user", "pharmacist", and "pharmacy technician" are interchangeable and refer to a person authorized to assign times of administration to medication(s) via an automated pharmacy dispensing system.

Example embodiments are described herein with reference to graphical user interfaces (GUIs), block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the GUIs, block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the GUIs, block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/BlueRay).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the GUIs, block diagrams and/or flowchart block or blocks. Accordingly, embodiments of the present invention may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

Figure 2A:
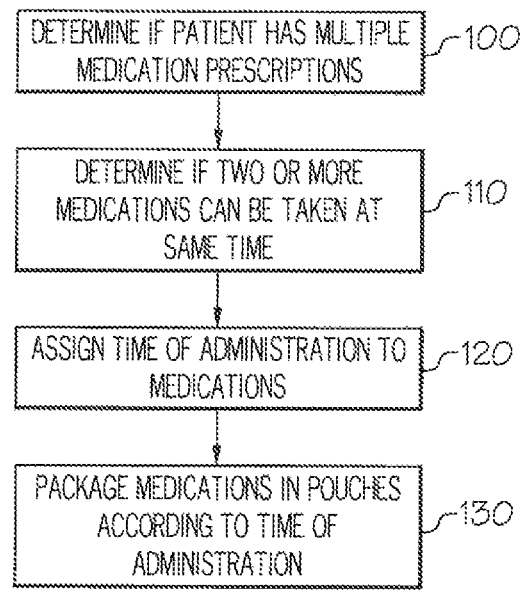
FIGS. 2A-2B are flowcharts of operations for packaging multiple medications in individual multi-dose medication pouches, according to some embodiments of the present invention.

Referring now to the figures, systems, methods, and computer program products for assigning a time of administration and packaging patient medications to be taken over a period of time, according to some embodiments of the present invention, will be described. Referring initially to FIG. 2A, a pharmaceutical dispensing system, such as the Parata PASS™ system (Parata, Inc., Durham, N.C.), is configured to determine if a patient has multiple medication prescriptions (Block 100), determine if any of the medications can be taken together (Block 110), and for medications that can be taken together, assign specific times of administration to the medications (Block 120). The pharmaceutical dispensing system is then configured to package medications to be taken at a same specific time in pouches, such as illustrated in FIG. 1. Determining if medications can be taken together may include accessing a database, knowledgebase, or other source of information to verify that there are no known unwanted or dangerous reactions that can occur when two medications are taken at the same time, and/or to verify that a particular patient is not known to have an allergic reactions to particular combinations of medications, etc. Alternatively, a pharmacist may be responsible for verifying that drugs with interactions are assigned specific times of administration that are appropriate for each drug. Medications that cannot be mixed with other medications can be packaged in a separate pouch or in a vial.

Figure 2B:
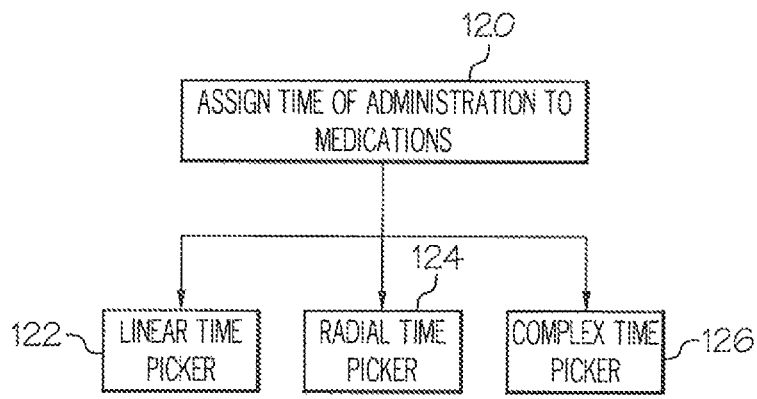

Assigning specific times of administration to the medications (Block 120) can be performed in numerous ways, as illustrated in FIG. 2B. In some embodiments, a linear time picker (Block 122) is utilized and in other embodiments a radial time picker (Block 124) is utilized, as will be described below. In some embodiments, a complex time picker (Block 126) is utilized, as will be described below. The complex time picker (Block 126) utilizes a calendar interface in combination with the linear time picker (Block 122) and/or radial time picker (Block 124).

According to embodiments of the present invention, a user, such as a pharmacist/pharmacy technician, receives multiple medication prescriptions for a patient and then, using various graphical user interfaces (GUIs) displayed within the display of a work station (820, FIG. 10) and described below in FIGS. 3-9, processes the prescriptions into batches. The batches are then filled by a packaging station (830, FIG. 10) of an automated pharmacy dispensing system. For example, the user uses the SIG information (physician provided information associated with a prescription, such as "take with food", "take two times a day", etc.), warnings, quantity, and days supply or schedule length for each prescription to process the patient's prescriptions into a batch. A typical batch packages a single patient's prescription for a 28-, 30-, or 31-day schedule, with each pouch (10, FIG. 1) containing all doses for all prescriptions to be administered at a specific date and time of day.

Referring to FIG. 3, a patient selector screen 200 that can be displayed within the display of a work station (820, FIG. 10) is illustrated. The illustrated patient selector screen 200 allows a user to locate and select patients such that specific times of administration can be assigned to their medication prescriptions. The illustrated patient selector screen 200 includes three portions: a patient name pane 202, a patient query pane 204, and a patient list navigation bar 206. The patient name pane 202 displays a list of patients having prescriptions to be filled. Each row 202a in the illustrated patient name pane 202 includes the name of a respective patient and the patient's birth date. Using the patient query pane 204, the user can search for patients by first or last name via boxes 204a, 204b, and using either partial or full spelling. The patient list navigation bar 206 allows the user to navigate between screens of patient query results using the arrow buttons 206a, 206b, as would be understood by one skilled in the art.

To assign times of administration to a patient's medications, the patient is selected from the patient name pane 202 of FIG. 3, which causes the patient information screen 300 (FIG. 4) to be displayed. The illustrated patient information screen 300 includes two panes or GUIs 310, 330 positioned adjacent to each other. GUI 310 contains information about a selected patient and his/her medication prescription(s). For example, in FIG. 4, information about five medication prescriptions 312a-312e is displayed for the selected patient. The medication prescription information includes a prescription number 314a, prescription medication name 314b, and a medication quantity (i.e., number of doses) 314c. Also included with each medication is a respective time picker GUI control 316a-316e that is responsive to user actuation for displaying a GUI in which the user can assign times of administration to the medication, as will be described below.

Each time picker GUI control 316a-316e displays a status of the assignment of times of administration for each respective medication. For example, in the illustrated embodiment of FIG. 4, time picker GUI controls 316a, 316b, 316c indicate that times of administration for the respective medication has been assigned. Time picker GUI control 316d indicates that the user has utilized a grid picker or calendar GUI (described below) to assign complex times of administration for the medication. Time picker GUI control 316e indicates that the assignment of times of administration has not been completed for this medication.

Figure 4:
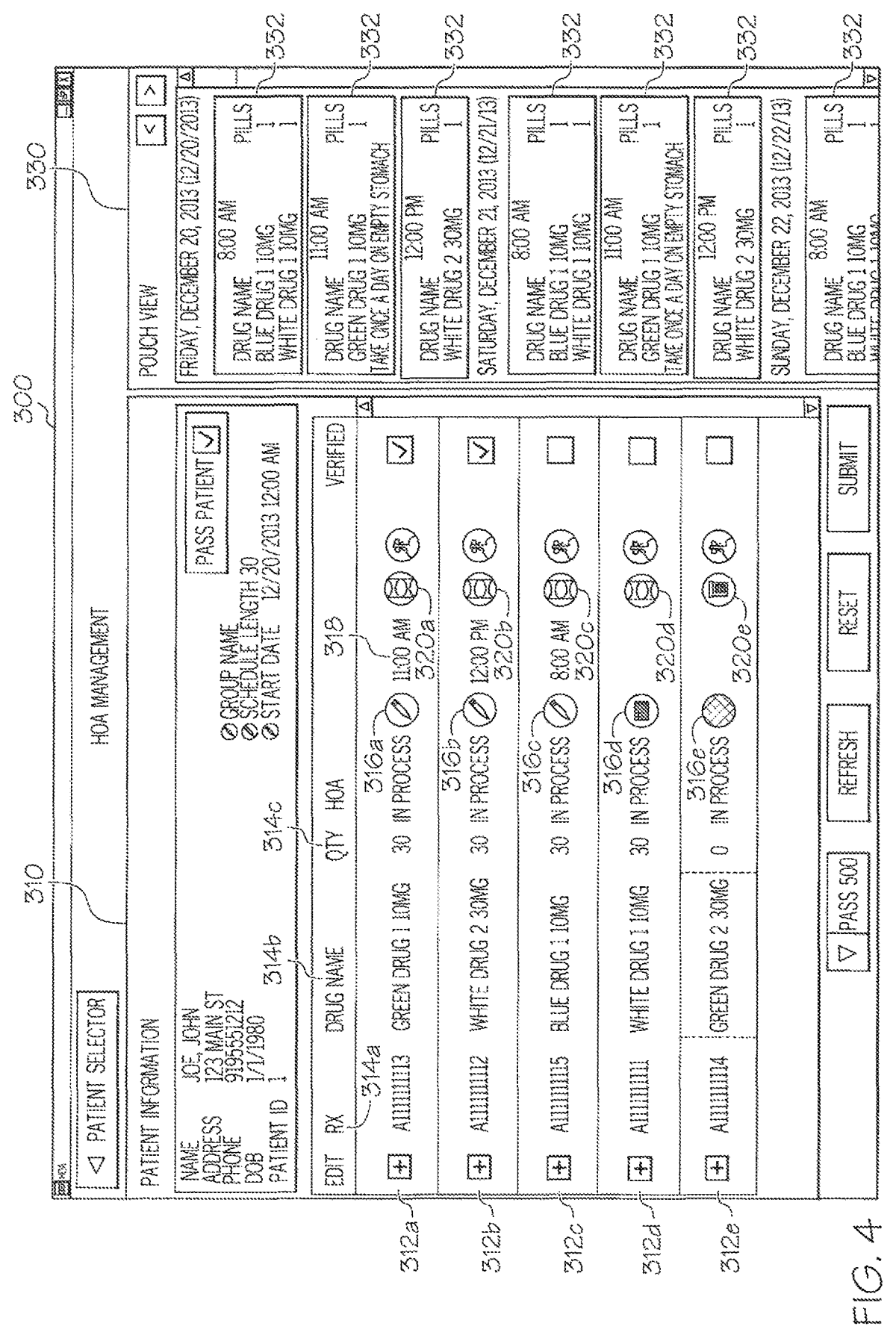

In the illustrated embodiment of FIG. 4, status icons 320a-320e are displayed with each respective medication 312a-312e. Status icons 320a-320d indicate that the medication will be packaged into respective pouches, such as the type of pouch 10 of FIG. 1, via a packaging station of an automated pharmacy dispensing system. Status icon 320e indicates that the medication will be packaged into a vial, for example via another type of automated/semi-automated pharmacy dispensing system.

GUI 330 illustrated in FIG. 4 displays how a patient's prescription(s) will be distributed into pouches based on the times of administration assigned thereto. In the illustrated embodiment, GUI 330 displays a respective representation 332 of each of the plurality of pouches. Each pouch representation 332 contains an identification of the medications contained in the corresponding pouch and a date and time of administration for the medications in the corresponding pouch.

Figure 5:
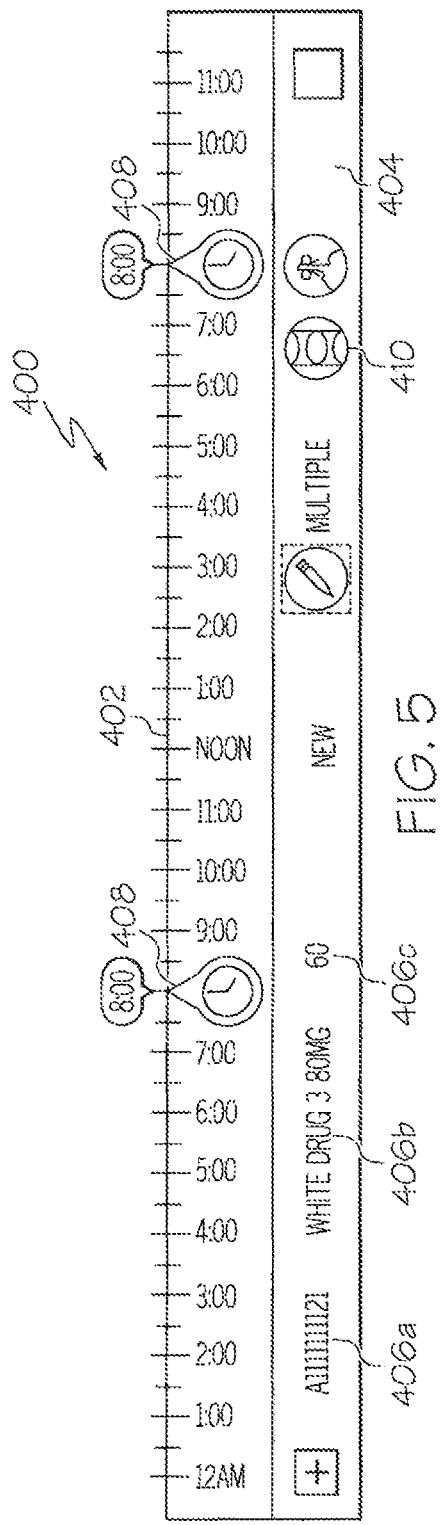

Referring now to FIGS. 5-9, the assignment of times of administration for medications will be described. FIG. 5 illustrates a linear time picker GUI 400 that is displayed when a user actuates a time picker GUI control, such as GUI controls 316a-316c of FIG. 4. The illustrated linear time picker GUI 400 is a one day time scale that includes a time line 402 representative of a twenty-four hour period. Information about a medication for which one or more times of administration per day are to be assigned is displayed beneath the time line 402 in area 404. In the illustrated embodiment the medication prescription information includes a prescription number 406a, prescription medication name 406b, and a medication quantity (i.e., number of doses) 406c.

The linear time picker GUI 400 includes one or more time indicators 408 that are positionable by a user at a respective time on the time line for assigning a time of administration of a dose of the medication. For example, the prescription for the medication may contain directions to take one pill every twelve hours. However, the prescription does not indicate what two hours of the day to take the medication. Using the linear time picker GUI 400, a user selects two specific times of day (i.e., 8:00 am and 8:00 pm) using the time indicators 408.

When two or more time indicators 408 are used to assign multiple times of administration in a day for a medication, the time indicators 408 may be slidably positionable along the time line 402 and movable together. For example, in the illustrated embodiment, movement of one of the time indicators 408 may automatically cause the other time indicator 408 to move to maintain the selected time period (i.e., twelve hours) therebetween. Thus, if it is desired to change the time of administration to 9:00 am and 9:00 pm, the user can move the time indicator 408 on the left to 9:00 am and the time indicator 408 on the right automatically moves to 9:00 pm to maintain the twelve hour interval therebetween. Similarly, the user can move the time indicator 408 on the right to 9:00 pm and the time indicator 408 on the left automatically moves to 9:00 am to maintain the twelve hour interval therebetween.

In the illustrated embodiment, the linear time picker GUI 400 displays a status icon 410 in area 404 that indicates that the medication will be packaged into respective pouches, such as pouch 10 of FIG. 1 via a packaging station of an automated pharmacy dispensing system. Once the user is finished with assigning the times of administration for a medication, the information can be saved by clicking anywhere on the linear time picker GUI 400. The linear time picker GUI then disappears and the user is returned to the patient information screen 300 (FIG. 4).

Figure 6:
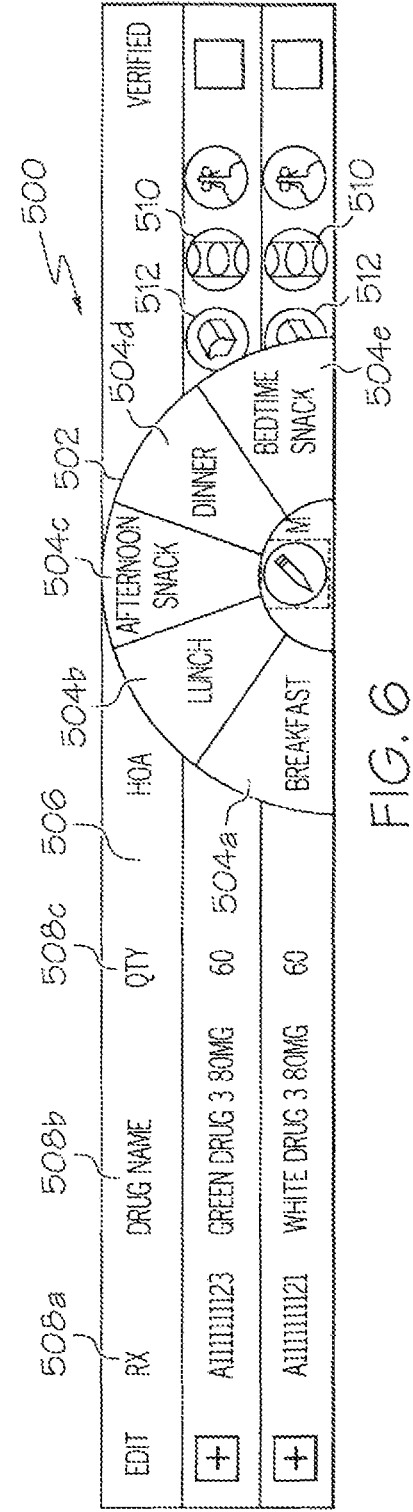

FIG. 6 illustrates a radial time picker GUI 500 that is displayed when a user actuates a time picker GUI control, such as GUI controls 316a-316c of FIG. 4. The illustrated radial time picker GUI 500 includes an arcuate display 502 of a one day time scale that has a plurality of food consumption times displayed as segments 504a-504e. Each segment 504a-504e corresponds to a respective food consumption time (i.e., a meal or snack time). In the illustrated embodiment, the arcuate display 502 includes a breakfast segment 504a, a lunch segment 504b, an afternoon snack segment 504c, a dinner segment 504d, and a bedtime snack segment 504e. The number and configuration of segments in the arcuate display 502 can be modified by a user (i.e., the segments are user-configurable). For example, a user may assign different names to the segments, may increase the number of displayed segments, or may decrease the number of displayed segments.

Each segment 504a-504e is responsive to user actuation for assigning a time of administration of a dose of the medication to a food consumption time. For example, a prescription may indicate that a medication is to be taken with food, but does not indicate when the medication is to be taken with food. The radial time picker GUI 500 allows a user to specifically identify a food consumption time (i.e., a meal or snack time) when a medication is to be taken.

The radial time picker GUI 500 assigns a "default" time to each named period, i.e. Breakfast=8:00 AM. If the default time of 8:00 AM is acceptable, then the radial time picker GUI 500 can be used to assign the dose time.

In the illustrated embodiment, the radial time picker GUI 500 displays information about a medication for which one or more times of administration per day are to be assigned in area 506. In the illustrated embodiment, the medication prescription information includes a prescription number 508a, prescription medication name 508b, and a medication quantity (e.g., number of doses or, alternatively, a number of pills that are assigned to a dose) 508c. In addition, area 506 includes a status icon 510 and a food icon 512 for each medication. The status icon 510 indicates that the medication will be packaged into respective pouches, such as pouch 10 of FIG. 1 via a packaging station of an automated pharmacy dispensing system. The food icon 512 indicates that, per the prescription, the medication must be taken with food.

Once the user is finished with assigning the times of administration for the medication, the information can be saved by clicking anywhere on the radial time picker GUI 500. The radial time picker GUI 500 then disappears and the user is returned to the patient information screen 300 (FIG. 4).

The linear time picker GUI 400 is used and for certain types of prescriptions, and the radial time picker GUI 500 is used for certain types of prescriptions. However, there are some types of prescriptions for which either may be utilized. Table 1 below summarizes the types of prescriptions for which the linear time picker GUI 400, the radial time picker GUI 500, or both may be utilized.

TABLE 1

| Dose Schedule or Delivery Method | Time Picker |
| --- | --- |
| Identical, single-pill doses every day | Linear Time Picker |
| Identical, single-pill doses every day and all dosage periods are default periods | Radial Time Picker |
| Identical single-pill doses every day but not all dosage periods are default periods OR Identical multiple-pill doses every day, whether by time or by period | Either |
| Prescription can not be packaged by automation (e.g., liquid, cream, or inhaler) | Either |

Figure 7:
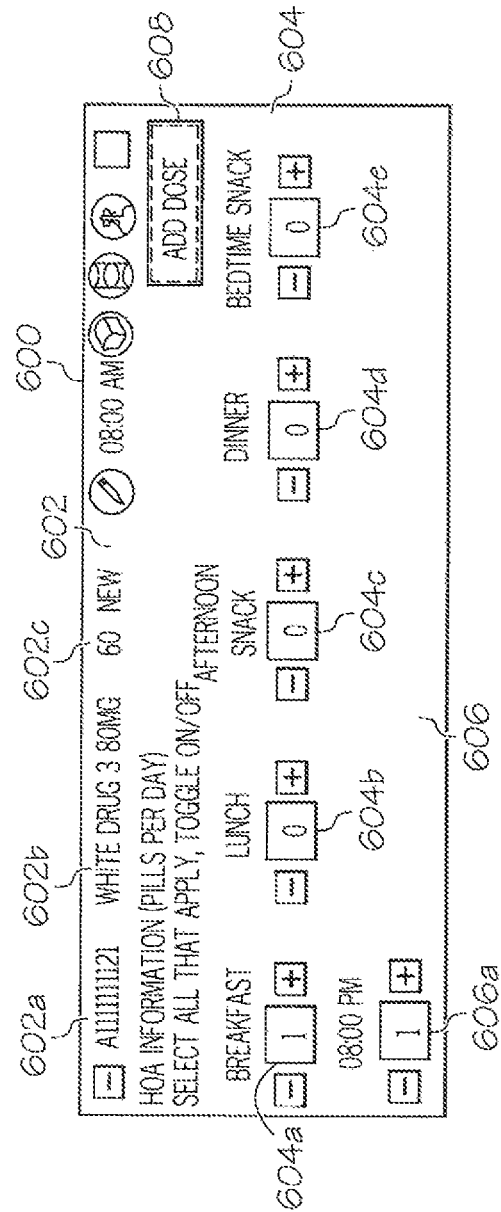

Some medication prescriptions require doses to be administered outside of typical time periods (e.g., meal times, etc.) and/or require multiple pills per dose. Referring to FIG. 7, GUI 600 allows a user to assign times of administration for medications that cannot be assigned using the linear time picker GUI 400 and the radial time picker GUI 500. The illustrated GUI 600 is divided into three sections 602, 604, and 606. Section 602 displays information about a medication for which one or more times of administration per day are to be assigned. In the illustrated embodiment the medication prescription information includes a prescription number 602a, prescription medication name 602b, and a medication quantity (i.e., number of doses) 602c. Section 604 displays a plurality of user input boxes 604a-604e that are associated with a food consumption time. For example, user input box 604a is associated with breakfast, user input box 604b is associated with lunch, user input box 604c is associated with afternoon snack, user input box 604d is associated with dinner, and user input box 604e is associated with bedtime snack. Section 606 displays a user input box 606a that is not associated with a food consumption time. For example, user input box 606a is associated with a specific time (i.e., 8:00 pm). There may be any number of user input boxes in sections 604, 606. Embodiments of the present invention are not limited to the illustrated number. GUI control 608 may be utilized to add additional user input boxes in sections 604, 606. For example, a user may activate GUI control 608 to add a mid-morning input box in section 604, a 12:00 PM input box in section 606, etc.

Each of the user input boxes 604a-604e and 606a are configured to receive a number representative of a quantity of the medication that is to be taken at a respective time of day or food consumption time. In the illustrated embodiment, the user has indicated that one pill of the medication is to be taken at breakfast and one pill of the medication is to be taken at 8:00 pm. Once the user is finished with assigning the times of administration for the medication, the information can be saved by clicking anywhere on the GUI 600. The GUI 600 then disappears and the user is returned to the patient information screen 300 (FIG. 4).

Figure 8:
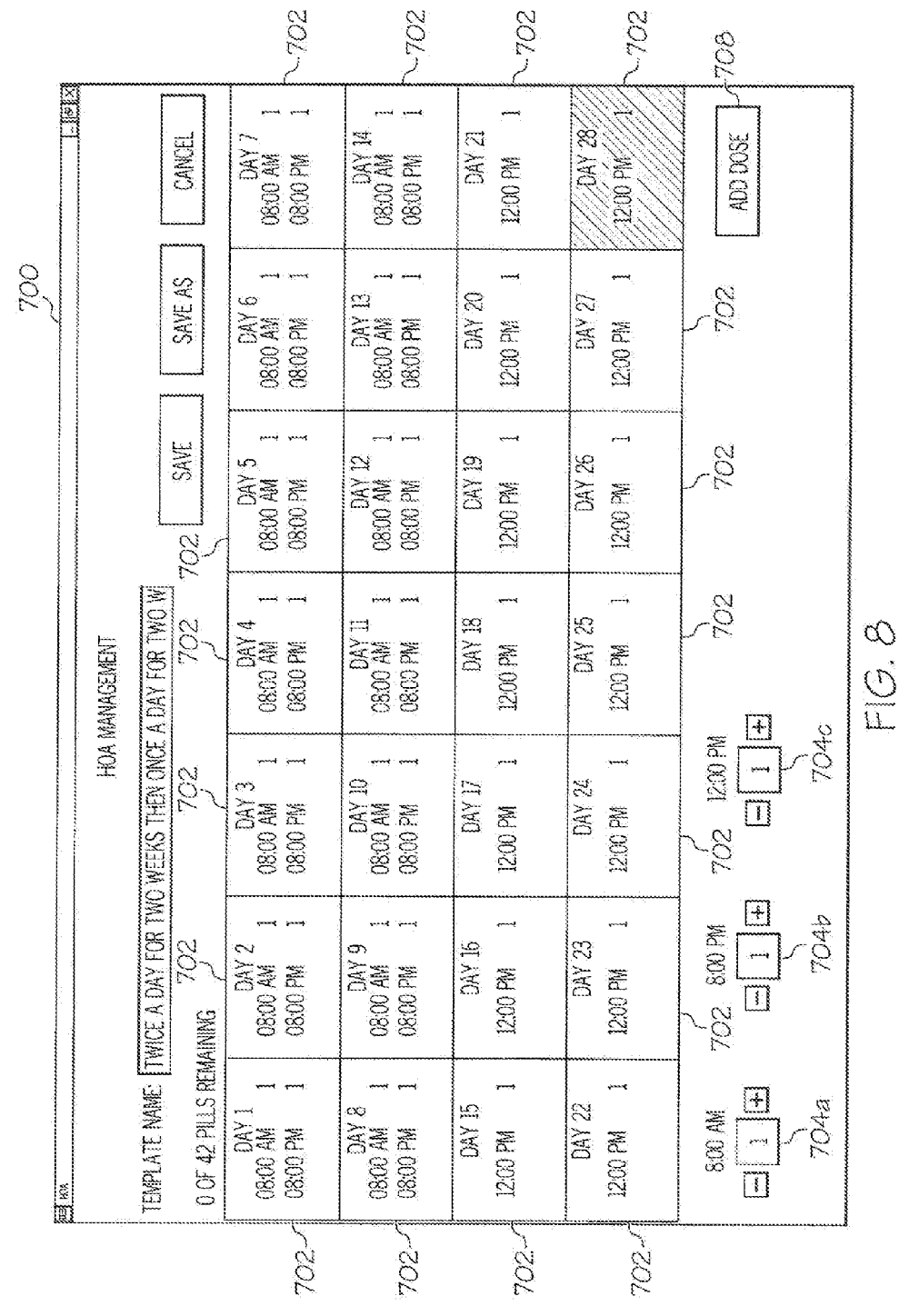

FIG. 8 illustrates a grid or calendar GUI 700 that allows a pharmacist/technician to assign times of administration that are irregular from day to day (e.g., taken every other day) or to prescription dosages that increase or decrease over time (i.e., dose titration). The illustrated calendar GUI 700 includes an array of blocks 702 that are representative of the days of a month. Each block 702 is configured to display one or more times of day and/or one or more food consumption times and a quantity of a medication that is to be taken at a respective time of day or food consumption time. The illustrated calendar GUI 700 also includes a plurality of user input boxes 704a-704c that are configured to receive a number representative of a quantity of a medication that is to be taken at a respective time of day. GUI control 708 may be utilized to add additional user input boxes. For example, a user may activate GUI control 708 to add an additional user input box for an additional time, such as 4:00 PM, etc.

To add one or more times of administration for one or more medications to a block 702, a user clicks on the respective block 702 to activate the block. The linear time picker GUI 400 and/or the radial time picker GUI 500 is then used, as described above, to assign times of administration for one or more medications. This is repeated for each block in the calendar GUI 700 as needed. In the illustrated calendar GUI 700 of FIG. 8, a user has assigned times of administration for a medication prescription with the instructions "take twice a day for two weeks then once a day for two weeks." Once the user is finished with assigning the times of administration for the medication, the information can be saved by clicking anywhere on the calendar GUI 700. The calendar GUI 700 then disappears and the user is returned to the patient information screen 300 (FIG. 4).

Figure 9:
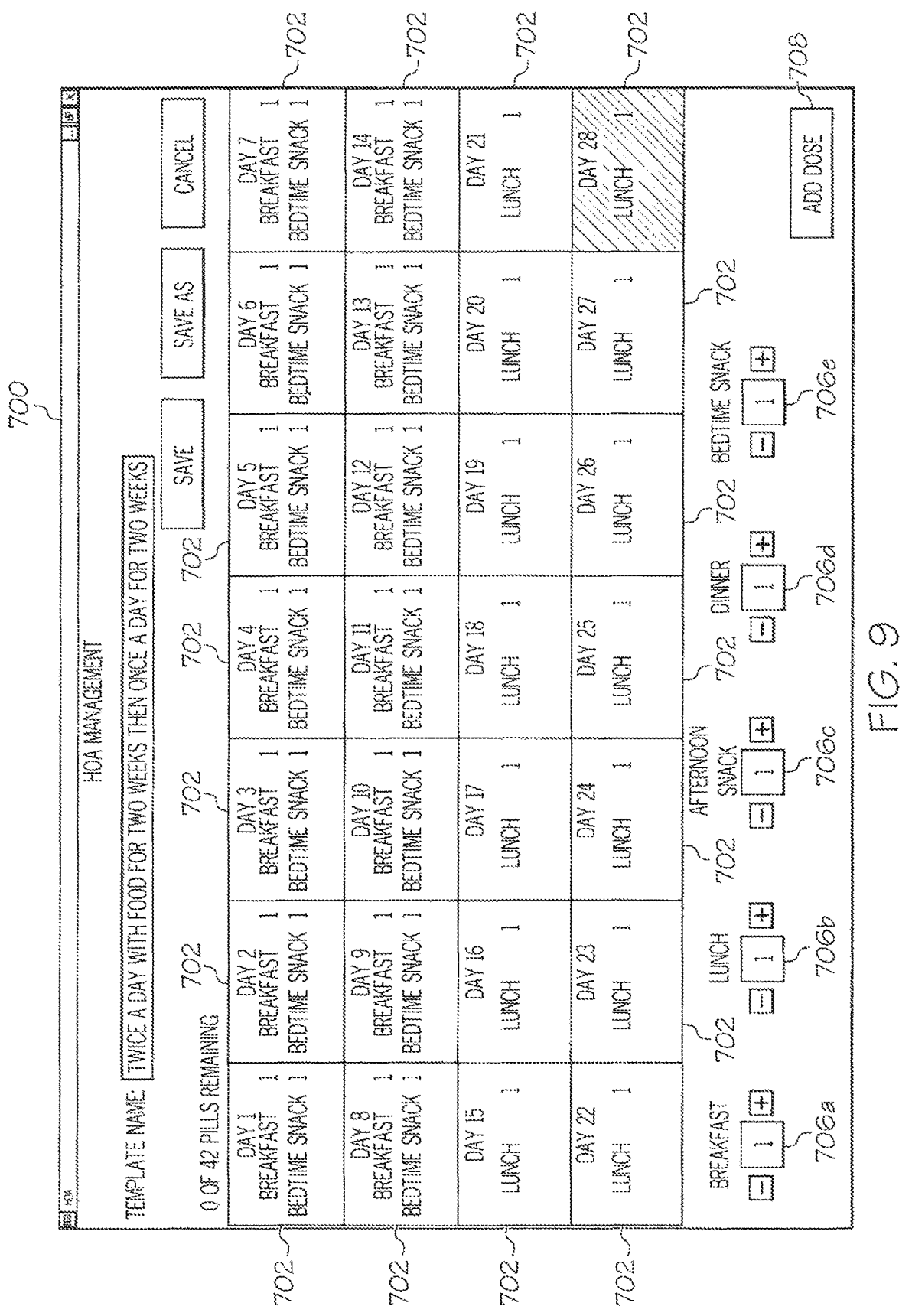

FIG. 9 illustrates the calendar GUI 700 of FIG. 8 where times of administration for a medication are assigned based on food consumption times. For example, the calendar GUI 700 in FIG. 9 includes a plurality of user input boxes 706a-706e that are configured to receive a number representative of a quantity of a medication that is to be taken at a respective food consumption time. In the illustrated calendar GUI 700 of FIG. 9, a user has assigned times of administration for a medication prescription with the instructions "take twice a day with food for two weeks, then once a day with food for two weeks."

Figure 10:
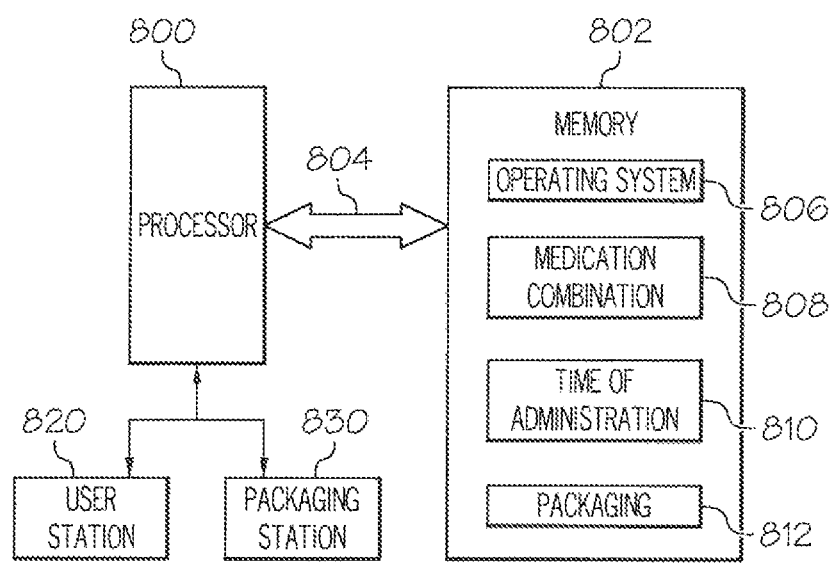
FIG. 10 is a block diagram that illustrates a software architecture for implementing the packaging of multiple medications in individual multi-dose medication pouches, according to some embodiments of the present invention.

FIG. 10 illustrates an exemplary processor 800 and memory 802 associated with an automated pharmacy dispensing system that may be utilized in implementing various embodiments of the present invention. However, embodiments of the present invention are not limited to a single processor and memory. Multiple processors and/or memory may be utilized, as would be understood by those skilled in the art.

The processor 800 and memory 802 may be utilized in conjunction with an automated pharmacy dispensing system to package prescribed patient medications to be taken over a period of time, as described above. The processor 800 communicates with the memory 802 via an address/data bus 804. The processor 800 may be, for example, a commercially available or custom microprocessor or similar data processing device. The memory 802 is representative of the overall hierarchy of memory devices containing the software and data used to perform the various operations described herein. The memory 802 may include, but is not limited to, the following types of devices: cache, ROM, PROM, EPROM, EEPROM, flash, SRAM, and DRAM.

As shown in FIG. 10, the memory 802 may hold various categories of software and data: an operating system 806, a medication combination module 808, a time of administration module 810, and a packaging module 812. The operating system 806 may manage the resources of one or more devices used to implement embodiments of the present invention and may coordinate execution of various programs (e.g., the medication combination module 808, the time of administration module 810, and the packaging module 812, etc.) by the processor 800. The operating system 806 can be any operating system suitable for use with a data processing system, such as IBM®, OS/2®, AIX® or z/OS® operating systems, Microsoft® Windows® operating systems, Android®, Unix or Linux™, etc.

The medication combination module 808 comprises logic for determining if a patient has multiple medication prescriptions (Block 100, FIG. 2A) and, in some embodiments, for determining if two or more of the medications can be taken together (Block 110, FIG. 2A). In other embodiments, the medication combination module 808 may only comprise logic for providing a drug name and an NDC associated therewith. In such embodiments, it is the pharmacist's responsibility to know and apply drug interaction restrictions about what medications can be taken together. The time of administration module 810 comprises logic for assigning times of administration to one or more medications (Block 120, FIGS. 2A-2B) via the various GUIs 200, 300, 400, 500, 600, and 700 described above. The packaging module 812 comprises logic for packaging medications in pouches according to assigned times of administration (Block 130, FIG. 2A).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method of packaging a plurality of prescribed patient medications to be taken over a period of time, the method comprising:
    displaying a first graphical user interface (GUI) within a display associated with a pharmaceutical dispensing system, wherein the first GUI contains prescription information for each of the medications that can be taken together, wherein the first GUI contains a time picker GUI control, wherein the time picker GUI control is responsive to user actuation for displaying a second GUI, wherein the second GUI comprises a one day time scale for assigning a time of administration for each of the medications, and wherein the second GUI comprises at least one of the following displayed adjacent the one day time scale: prescription number, medication name, and medication quantity;
    for each medication, displaying the second GUI in response to user actuation of the time picker GUI control, and assigning one or more daily times of administration for the medication in response to user input via the one day time scale, wherein the one day time scale comprises a time line representative of a twenty-four hour period, and wherein the second GUI comprises one or more time indicators, each time indicator slidably positionable by a user at a respective time on the time line for assigning a time of administration of a dose of each medication; and
    packaging individual doses of the medications in a plurality of pouches via the pharmaceutical dispensing system, wherein each pouch contains an individual dose of a plurality of the medications having the same daily time of administration, and wherein each pouch displays an identification of the medications contained therein and a date and time of administration for the medications.

2. The method of claim 1, further comprising displaying a third GUI adjacent to the first GUI, wherein the third GUI displays a representation of each of the plurality of pouches, wherein each pouch representation contains an identification of the medications contained in the corresponding pouch and a date and time of administration for the medications in the corresponding pouch.

3. The method of claim 1, wherein the one or more time indicators comprise a pair of time indicators spaced apart by a selected time period, and wherein movement of one of the time indicators in a direction automatically causes the other time indicator to move in the same direction to maintain the selected time period therebetween.

4. The method of claim 1, further comprising a fourth GUI that comprises an array of blocks representative of the days of a month, wherein each block is configured to display one or more times of day and/or one or more food consumption times and a quantity of a medication to be taken at a respective time of day or food consumption time, and wherein a user assigns a time of administration of a dose of a respective medication for one or more of the blocks via the second GUI.

5. A pharmaceutical dispensing system, comprising:
    a user station;
    a packaging station configured to selectively package individual doses of medication into customized packaging;
    a processor connected to the user station and the packaging station; and
    a memory that stores instructions that, when executed by the processor, cause the processor to perform operations comprising:
    displaying a first graphical user interface (GUI) within a display associated with the user station, wherein the first GUI contains prescription information for each of the medications that can be taken together, wherein the first GUI contains a time picker GUI control, wherein the time picker GUI control is responsive to user actuation for displaying a second GUI, wherein the second GUI comprises a one day time scale for assigning a time of administration for each of the medications, and wherein the second GUI comprises at least one of the following displayed adjacent the one day time scale: prescription number, medication name, and medication quantity;
    for each medication, displaying the second GUI in response to user actuation of the time picker GUI control, and assigning one or more daily times of administration for the medication in response to user input via the one day time scale, wherein the one day time scale comprises a time line representative of a twenty-four hour period, and wherein the second GUI comprises one or more time indicators, each time indicator slidably positionable by a user at a respective time on the time line for assigning a time of administration of a dose of each medication; and
    packaging individual doses of the medications in a plurality of pouches via the packaging station, wherein each pouch contains an individual dose of a plurality of the medications having the same daily time of administration, and wherein each pouch displays an identification of the medications contained therein and a date and time of administration for the medications.

6. The pharmaceutical dispensing system of claim 5, further comprising displaying a third GUI adjacent to the first GUI, wherein the third GUI displays a representation of each of the plurality of pouches, wherein each pouch representation contains an identification of the medications contained in the corresponding pouch and a date and time of administration for the medications in the corresponding pouch.

7. The pharmaceutical dispensing system of claim 5, wherein the one or more time indicators comprise a pair of time indicators spaced apart by a selected time period, and wherein movement in a direction of one of the time indicators automatically causes the other time indicator to move in the same direction to maintain the selected time period therebetween.

8. The pharmaceutical dispensing system of claim 5, further comprising a fourth GUI that comprises an array of blocks representative of the days of a month, wherein each block is configured to display one or more times of day and/or one or more food consumption times and a number of pills that are to be taken at a respective time of day or food consumption time, and wherein a user assigns a time of administration of a dose of a respective medication for one or more of the blocks via the second GUI.

9. A computer program product, comprising a non-transitory computer readable storage medium having encoded thereon instructions that, when executed on a processor, causes the processor to perform operations comprising:
  displaying a first graphical user interface (GUI) within a display associated with a pharmaceutical dispensing system, wherein the first GUI contains prescription information for each of the medications that can be taken together, wherein the first GUI contains a time picker GUI control, wherein the prescription information for each medication comprises an identification of the medication, a quantity of the medication, and a dose amount for the medication, wherein the time picker GUI control is responsive to user actuation for displaying a second GUI, wherein the second GUI comprises a one day time scale for assigning a time of administration for each of the medications, and wherein the second GUI comprises at least one of the following displayed adjacent the one day time scale: prescription number, medication name, and medication quantity;
  for each medication, displaying the second GUI in response to user actuation of the time picker GUI control, and assigning one or more daily times of administration for the medication in response to user input via the one day time scale, wherein the one day time scale comprises a time line representative of a twenty-four hour period, and wherein the second GUI comprises one or more time indicators, each time indicator slidably positionable by a user at a respective time on the time line for assigning a time of administration of a dose of each medication; and
  packaging individual doses of the medications in a plurality of pouches via the pharmaceutical dispensing system, wherein each pouch contains an individual dose of a plurality of the medications having the same daily time of administration, and wherein each pouch displays an identification of the medications contained therein and a date and time of administration for the medications.

* * * * *